United States Patent
Kibayashi et al.

(10) Patent No.: US 6,608,080 B1
(45) Date of Patent: Aug. 19, 2003

(54) MORPHAN DERIVATIVES OR SALTS THEREOF AND MEDICINAL COMPOSITIONS CONTAINING THE SAME

(75) Inventors: Chihiro Kibayashi, Tokyo (JP); Takeshi Miyata, Kumamoto (JP); Kazuo Takahama, Kumamoto (JP); Hidenao Fukushima, Ibaraki (JP)

(73) Assignee: Hisamitsu Pharmaceutical Co., Ltd., Saga (JP)

( * ) Notice: Subject to any disclaimer, the term of this patent is extended or adjusted under 35 U.S.C. 154(b) by 0 days.

(21) Appl. No.: 09/913,666

(22) PCT Filed: Feb. 17, 2000

(86) PCT No.: PCT/JP00/00897
§ 371 (c)(1),
(2), (4) Date: Aug. 16, 2001

(87) PCT Pub. No.: WO00/48999
PCT Pub. Date: Aug. 24, 2000

(30) Foreign Application Priority Data

Feb. 18, 1999 (JP) ............................................ 11-039374

(51) Int. Cl.[7] ..................... A61K 31/439; C07D 221/22
(52) U.S. Cl. ...................... 514/299; 546/112; 514/299
(58) Field of Search ........................... 546/112; 514/299

(56) References Cited

U.S. PATENT DOCUMENTS 4,086,227 A * 4/1978 Adelstein et al. ............. 260/239
5,498,614 A * 3/1996 Desai et al. .................. 546/112

FOREIGN PATENT DOCUMENTS

| EP | 0018077 | | 10/1980 | |
| GB | 956613 | | 4/1964 | |
| US | WO-9945925 | * | 9/1999 | ......... A61K/31/435 |
| WO | 97/48681 | | 12/1997 | |

OTHER PUBLICATIONS

Bosch, Joan et al. Synthesis of 2–Azabicyclo[3.3.1 Nonanes. Heterocycles (1980) vol. 14, pp. 505–529.*
Bosch, Joan et al, "Synthesis of 2–Azabicyclo[3.3.1] Nonanes" Heterocycles (1980) vol. 14 (4), pp 505–529.*
Goldinger, A. et al., "Inhibition of Glycine and GABA Receptor Binding by Several Opiate Agonists and Antagonists" General Pharmacology, 1981, vol. 12, No. 6, pp. 477–479.
Quirante, Josefina et al. "A Radical Route to Morphans. Synthesis and Spectroscopic Data of the 2–Azabicyclo [3.3.1] Nonane" Heterocycles (1999) vol. 50 No. 2, pp. 731–738.
Yamazaki, Naoki et al. "Nucleophilic Alylation on Anti–Bredt Iminium Ions. Facile Entry to the Synthesis of 1–Alkyated 2–Azabicyclo [3.3.1] Nonanes (Morphans) and 5–Azatricyclo [6.3.1.0] Dodecane" J. Org. Chem. (1997), vol. 62, pp. 8280–8281.
Bosch, Joan et al. Synthesis of 2–Azabicyclo [3.3.1] Nonanes. Heterocycles (1980) vol. 14, pp. 505–529.
S.F. Martin et al. "Novel Intramolecular [4+2] Cycloaddition Reactions" J. Am. Chem. Soc. (1980), vol. 102, No. 16,pp.5274–5279.
M.W. Cronyn "2–Azabicyclo [3.3.1] Nonane" J. of Organic Chem. (1949), vol. 14, pp.1013–1018.

* cited by examiner

Primary Examiner—Alan L. Rotman
Assistant Examiner—Janet L Coppins
(74) Attorney, Agent, or Firm—Peter F. Corless; John B. Alexander; Edwards & Angell, LLP (57) ABSTRACT

Medicinal compositions having an effect of regulating the activation of glycine receptor and novel morphan derivatives. Medicinal compositions comprising morphan derivatives or its salts and a pharmaceutically acceptable carrier. These compositions potentiate or inhibit the activation of glycine receptor, which makes them useful as drugs for the central nervous system. Novel 1- and/or 2-substituted morphan derivatives (2-azabicyclo[3.3.1]nonane derivatives) or salts thereof.

4 Claims, 2 Drawing Sheets

MORPHAN DERIVATIVES OR SALTS THEREOF AND MEDICINAL COMPOSITIONS CONTAINING THE SAME

TECHNICAL FIELD

The present invention relates to regulators for the activation of glycine receptors comprising morphan derivatives or salts thereof. The described regulators potentiate or inhibit the activation of the receptor (glycine receptors) which is specifically bound with the inhibitory neurotransmitter glycine. More particularly, the potentiators for the activation of glycine described in the present invention are useful as drugs for the treatment of convulsive seizures or epileptic seizures and as anesthetics. Further, the inhibitors for the activation of glycine receptors described in the present invention are useful as drugs for the treatment of nonketotic hyperglycinemia, and as antitussives or central nervous system stimulants. The regulators for the activation of glycine receptors described in the present invention are also useful as pharmacological tools for analyzing the function of these receptors.

The present invention also relates further to the medicinal compositions containing morphan derivatives represented by the formula (1) or salts thereof and pharmaceutically acceptable carrier thereof. Further, the present invention relates to novel compounds comprising morphan derivatives or salts thereof represented by the formula (2).

BACKGROUND ART

Glycine is a major inhibitory neurotransmitter of the central nervous system and is distributed mainly in the medulla and the spinal cord. This is in sharp contrast to another inhibitory neurotransmitter, Y-aminobutyric acid (GABA), which is distributed in the upper central region. With regard to the GABA receptor and the GABAergic neurotransmitter mechanism, a binding site, which is modified by antianxiety drugs, anesthetics, anticonvulsants or hypnotics, acting on the GABA receptor-ionchannel complex (hereinafter designated as the GABA receptor) has been elucidated (Ann. Rev. Neurosci., 17, 569–602, 1994); and drugs targeting the GABA receptor have been developed extensively. The importance of the GABA receptor for maintaining the functions of the psychoneural system has been recognized, and its physiological roles and pharmacological significance, including its regulatory mechanism, have been thoroughly elucidated. On the contrary, with regard to drugs modifying the functions of the glycine receptors, such as the known glycine receptors antagonist, strychnine, only a small number of drugs has been found. Owing to this fact, the pharmacological significance of glycine receptors has not been well elucidated and even their physiological role remains unknown.

With respect to the function and structure of the glycine receptor, in addition to results of studies on the electrophysiological properties of the glycine receptor [Nature, 277, 234–236; Nature, 305, 805–808, 1983; J. Physiol. (Lond.), 385, 243–286, 1987; J. Physiol. (Lond.), 435, 303–331, 1991], the molecular structure of glycine receptors has been estimated. This has been accomplished as a result of introducing molecular biological studies [J. Physiol. (Paris), 88, 243–248, 1994; Curr. Opin. Neurobiol., 5, 318–323, 1995], and the actual features of the glycine receptor as a functional molecule have been determined. Based on these findings, the relationship between the glycine receptor and nervous diseases has recently been elucidated from the clinical standpoint. For example, it has been reported that the causes of diseases resulting in convulsive symptom in glycine receptors deficient mice (Nature, 298, 655–657, 1982) and familial "startle disease" are both due to mutations in the gene coding for the glycine receptors (J. Biol. Chem., 269, 18739–18742, 1994; Trends Neurosci., 18, 80–82, 1995). Since these nervous system diseases are caused by functional disorders in the glycine receptors in the central nervous system networks, drugs which can potentiate the activation of the glycine receptors, help them to recover the original networks of the central nervous system. This is done by activating the remaining small numbers of normally functioning glycine receptors more strongly in vivo. As a result, this is expected to ameliorate or treat the symptoms of nervous diseases.

An example of another nervous diseases involving the glycine receptors is nonketotic hyperglycinemia, which is a fatal idiopathic abnormal metabolic disease (The Metabolic Basis of Inherited Diseases, McGraw-Hill, N.Y., pp. 743–753, 1989). Nonketotic hyperglycinemia is characterized by the accumulation of glycine in the blood and cerebrospinal fluid, which is caused by a defect in an enzyme of the glycine cleavage system. It is a disease resulting in a severe nervous disorder as a result of hyperactivation of the glycine receptors. Heretofore, drugs which suppress the activation of glycine receptors have been expected to reduce the neurotoxicity induced by glycine. Clinical cases in which the above-mentioned strychnine has been applied as a drug for treatment of such diseases have been reported (Helv. Paediat. Acta, 32, 517–525, 1977; Pediatrics, 63, 369–373, 1979; Helv. Paediat. Acta, 34, 589–599, 1979). However, massive doses of strychnine produce strong systemic toxicity, and small doses of strychnine also result in toxic symptoms, as well as accumulation. It is a drug which is very difficult to use in clinical practice. Consequently, the development of very safe activation inhibitors as alternatives to strychnine is strongly desired.

Further, recent reports on the relationships between glycine receptors and central nervous system agonists have attracted attention. Firstly, it has been demonstrated that a known inhalation general anesthetic agent, enflurane, recognizes a specific amino acid residues in the glycine receptors and potentiates the activation of the receptor (Nature, 389, 385–389, 1997). Since the mechanism of action of anesthetic agents has been said to be a non-selective action such as affecting the fluidity of the nerve cell membrane, knowledge about regulation of the activation by binding the anesthetic agent with the receptor suggests the fact that this is an action against a target with high specificity in the central nervous system. Consequently, drugs which can potentiate the activation of glycine receptors are expected to be candidates for anesthetic agents. Secondly, it has been reported that a common mechanism of action of large numbers of central antitussives, such as dextromethorphan, is to suppress the activation of glycine receptors (Br. J. Pharmacol., 120, 690–694, 1997; Meth. Find. Exp. Clin. Pharmacol., 20, 125–132, 1998). Antitussives are developed to provide remission or suppression of the pathologic cough which accompanies the pathological conditions of respiratory diseases; and, at present, large numbers of narcotic and nonnarcotic central antitussives are used as drugs. However, even though the former have strong antitussive action, their use is limited due to their narcotic action, and the latter produce insufficient antitussive effects. Consequently, the development of ideal antitussives with fewer adverse effects and sufficient efficacy is strongly desired; and inhibitors of the activation of glycine receptors are expected to be candidate drugs for antitussives with reliable effects.

In addition, agents developed as drugs can be utilized as pharmacological tools, and are used for analyses of mechanisms of regulation of various receptors or ion channels. Further, the strychnine mentioned above has been commonly used only for analyses of function of the glycine receptor. Consequently, drugs for regulating the activation of the glycine receptors are expected to be a useful pharmacological tool in order to understand the regulatory mechanisms of the physiological roles of these receptors.

A known example of a morphan derivative is the five-membered ring morphine and immunosuppressant FR901483. Various morphan derivatives have been reported as a result of studies on the synthesis of these compounds. For example, N. Yamazaki, et al., J. Org. Chem., 62, 8280–8281, 1997, describe the synthesis of 1-lower alkyl-morphan derivatives.

As explained above, knowledge that the glycine receptors is involved in neurological diseases, and that known drugs have a mechanism of action for regulating the function of glycine receptors, indicates that the glycine receptors is a hopeful new target for drug development, as well as for development of drugs having novel mechanisms of action. In addition, if drugs modifying the function of glycine receptors can be developed, completely new therapeutic methods for various neurological diseases can be provided.

Consequently, the present invention results in morphan derivatives which are useful as novel regulators for the activation of glycine receptors.

DISCLOSURE OF THE INVENTION

The present inventors conducted thorough investigation to solve the above described problems, and found for the first time that morphan derivatives or salts thereof, in particular, morphan derivatives (2-azabicyclo[3.3.1]nonane derivatives) or salts thereof represented by the formula (1) potentiate or inhibit the activation of glycine receptor, and have completed the present invention.

Thus, the present invention relates to a medicinal composition containing morphan derivatives or salts thereof having a regulating action for the activation of glycine receptor and pharmaceutically acceptable carrier thereof, methods of treatment for various diseases caused by disorder of the activation of glycine receptor by using the above described medicinal compositions and use of morphan derivatives or salts thereof to produce the above medicinal composition.

In more detail, the present invention relates to medicinal compositions containing morphan derivatives or salts thereof represented by the following formula (1) and pharmaceutically acceptable carrier thereof:

(1)

wherein, $R_1$ shows a hydrogen, an optionally substituted lower alkyl group, an optionally substituted alkenyl group, an optionally substituted aromatic aliphatic group or an alkylene group having an optional substitution group which can form a ring together with adjacent atoms and $R_2$; and, $R_2$ shows a hydrogen, an optionally substituted lower alkyl group or an optionally substituted alkenyl group.

In further more detail, the present invention relates to drugs to regulate the activation of glycine receptor, containing morphan derivatives or salts thereof. The present invention also relates to morphan derivatives or salts thereof represented by the following formula (2) or salts thereof:

(2)

wherein, $R_1$ shows a hydrogen, an optionally substituted lower alkyl group, an optionally substituted alkenyl group, an optionally substituted aromatic aliphatic group or an alkylene group having an optional substituent which can form a ring together with adjacent atoms and $R_2$; and, $R_2$ shows a hydrogen, an optionally substituted lower alkyl group or an optionally substituted alkenyl group;

however, $R_2$ is not a hydrogen or an unsubstituted lower alkyl group when $R_1$ is a hydrogen, and a substituent on a lower alkyl group, an alkenyl group and an aromatic aliphatic group in $R_1$ and $R_2$ is not a hydroxyl group, and is not a propylene group when $R_1$ is an alkylene group.

The present invention further relates to medicinal compositions containing morphan derivatives or salts thereof and pharmaceutically acceptable carrier thereof, having an regulating action for the activation of glycine receptor or having a central nervous action, use of morphan derivatives or salts thereof represented by the above formula (2) to produce the above described medicinal compositions having a regulating action for the activation of glycine receptor or having a central nervous action, and also methods for treatment or prevention of diseases caused by disorder of the activation of glycine receptor, preferably diseases on central nervous system, comprising administrating an effective amount of a morphan derivative or a salt thereof represented by the above described formula (2).

BRIEF DESCRIPTION OF THE DRAWINGS

The drawings illustrated hereinunder compose a part of the present invention and are intended to disclose the present invention in more detail, however it should be understood that the present invention is not limited within subjects disclosed by these drawings.

BEST MODE FOR CARRYING OUT THE INVENTION

The lower alkyl group in the above described formulas (1) and (2) is a linear or branched alkyl group having 1–15 carbon atoms, preferably 1–10 carbon atoms, and more preferably 1–7 carbon atoms, including a group such as methyl, ethyl, n-propyl, isopropyl, n-butyl and isobutyl group. The alkenyl group is a linear or branched group with one or more carbon-carbon unsaturated bonds and having 2–20 carbon atoms, preferably 2–10 carbon atoms, and more preferably 2–7 carbon atoms, including a group such as allyl, 3-methylallyl and 3,3-dimethylallyl group. The aromatic aliphatic group is a group having 7–45 carbon atoms, preferably 7–21 carbon atoms, and more preferably 7–12 carbon atoms, and preferably the above described lower alkyl group bonded with a group comprising 1–5, preferably 1–2 monocyclic or condensed cyclic aromatic rings, including a group such as benzyl, phenethyl and α-naphthylmethyl group, and preferably benzyl group.

The alkylene group which can form a ring together with $R_2$ and adjacent atoms is a linear or branched group having 2–20 carbon atoms, preferably 2–10 carbon atoms, and more preferably 2–7 carbon atoms, forming a four or more membered ring together with a carbon atom adjacent to $R_1$ and a nitrogen atom adjacent to $R_2$. A preferable alkylene group includes, for example, propylene group and butylene group.

The lower alkyl group, alkenyl group, aromatic aliphatic group and alkylene group in the above described formulas (1) and (2) may appropriately be substituted. Such a substituent may be any group so long as it does not impair the regulating action for the activation of glycine acceptor and includes the above mentioned lower alkyl group such as methyl, ethyl, n-propyl, isopropyl, n-butyl and isobutyl group and alkenyl groups, as well as a halogen atom, a hydroxyl group and a lower alkoxy group such as methoxy and ethoxy group, derived from the above mentioned lower alkyl group.

Further, the morphan derivatives as a drug to regulate the activation of glycine receptor are not limited to the compounds represented by the above described formulas (1) and (2), and any morphan derivative may be included so long as it has a function as a drug to regulate the activation of glycine receptor. An object of the present invention is to provide a novel drug to regulate the activation of glycine receptor, and in more detail, the present invention found for the first time that morphan derivatives or salts thereof has a regulating action for the activation of glycine receptor, and thus the drugs to regulate the activation of glycine receptor of the present invention are not limited to the morphan derivatives and salts thereof represented by the above described formulas (1) and (2) and should include any morphan derivative or a salt thereof having a regulating action for the activation of glycine receptor.

The morphan derivatives of the present invention, more specifically, the morphan derivatives represented by the above described formulas (1) and (2) may optionally be converted to salts thereof, and the salts thus formed may further be converted to free bases thereof. The salt of the present invention includes, a salt of mineral acid such as hydrochloric acid, hydrobromic acid, hydroiodic acid, sulfuric acid, nitric acid and phosphoric acid, or a salt of organic acid such as acetic acid, maleic acid, fumaric acid, citric acid, oxalic acid, succinic acid, tartaric acid, malic acid, mandelic acid, methanesulfonic acid, p-toluenesulfonoic acid and 10-camphorsulfonic acid.

The morphan derivatives of the present invention may optionally take a solvated form such as hydrate.

Some of the morphan derivatives and salts thereof of the present invention represented by the above described formula (1) are novel compounds. Thus the present invention provides such novel chemical substances consisting of novel 1- and/ or 2-substituted morphan derivatives (2-azabicyclo[3.3.1]nonane derivatives) or salts thereof and in more detail, novel morphan derivatives and salts thereof represented by the above described formula (2).

Preferable embodiment of the morphan derivatives of the present invention will be typically shown in the Examples hereinunder, however, the present invention should not be limited to these illustrative examples.

The morphan derivatives of the present invention, more specifically, the morphan derivatives represented by the above formulas (1) and (2) can be produced by various methods such as a method substituting the hydrogen atom on the nitrogen atom at the position 2 of 2-azabicyclo[3.3.1]nonane. For example, they can be produced by the method shown by the following reaction scheme;

That is, in process 1,2-azabicyclo[3.3.1]nonane represented by the formula (3) is reacted with formalin, acetaldehyde or allylbromide in a polar solvent such as methanol and dimethoxyethane to yield a derivative represented by the above formulas (1) and (2) of the present invention.

The compounds and salts thereof of the present invention may also be produced according to the method disclosed in the above described J. Org. Chem., 62, 8280–8281 (1997).

The medicinal composition having an effect on the regulation of the activation of glycine receptors described in the present invention is useful as a drug for the treatment and prevention of various diseases caused by failure of the activation of the glycine receptors. More particularly, it is useful as a central nervous system acting drug involving the glycine receptors. More concretely, with regard to drugs which have potentiation action on glycine receptors, it is useful as a drug for treatment of convulsive seizures and epileptic seizures or as an anesthetic. With regard to drugs having inhibitory actions on glycine receptor, it is useful as a drug for treatment of nonketotic hyperglycinemia, as an antitussive or as a central nervous system stimulant. In addition, the drugs for regulating the activation of glycine receptors described in the present invention are useful as pharmacological tools for analyzing the functions of glycine receptors.

The morphan derivatives or salts thereof described in the present invention, and most especially the medicinal compositions containing morphan derivatives represented by the aforementioned formulas (1) or (2) (or salts thereof) can be formulated for various pharmaceutically acceptable formulations by combining them as active ingredient with conventionally used general fillers. In cases in which the morphan derivatives, or salts thereof, are used as activation potentiators or activation inhibitors of glycine receptors, they can be administered in any dosage form by either oral or parenteral routes. Examples of oral administration forms are capsules, tablets, syrup, granules, fine granules and powders. Examples of parenteral administration forms are external preparations such as cataplasms, ointments, gels, creams, gel creams, lotions, liniments, aerosols, plasters, suppositories, ophthalmic solutions, nasal drops, buccals and fomentations, and injections. The above exemplified preparations for oral or parenteral administration can be dispensed according to the known vehicles and known formulations. For example, these include references as follows: 1) "General Technology for New Preparation Development System—Edition on Vehicles and Additives", Published: Jul. 12, 1985, R & D Planning Publisher; 2) "Today's Dermatologic External Preparations", Published: May 15, 1981 (1st Ed.), Nanzando Publisher; 3) Manual for the Japanese Pharmacopoeia 11th Ed., Published: Jul. 18, 1986, Publisher Hirokawa; 4) Practical Pharmacy I and II—Dispensing Pharmacy and Galenical Pharmacy, Published: 1988, Publisher: Nihon Kogyo Gijutsu Renmei; and 5) Known documents such as Related references, Patent Publications and Journals published prior to filing date of the present invention.

Concrete preparation for pharmaceutical preparations will be explained later in details.

Preparations for oral administration can be prepared, for example, as follows. Morphan derivatives or salts thereof and organic acid (for example, citric acid, ascorbic acid, fumaric acid, tartaric acid, succinic acid, malic acid, adipic acid, etc.) or antacid (for example, sodium hydrogen carbonate, calcium hydrogen phosphate, magnesium metasilicate aluminate, magnesium hydroxide, synthetic hydrotalcite, etc.) are properly mixed to prepare medicinal composition. The thus prepared medicinal composition or admixed additives therewith is microcapsulated by the known methods. Alternatively, suitable binders, lubricants, disintegrators, fillers, disintegration regulators, plasticizers, coloring agents, flavors, etc. are optionally added to the said medicinal composition to prepare tablets, granules or fine granules. Further, these preparations are treated with sustained release coating membranes, for example water insoluble polymer such as ethyl cellulose, aminoalkylmetacrylate copolymer, polyvinyl acetate and polyethylene, enteric coating polymer such as cellulose acetate phthalate, hydroxypropyl methyl cellulose phthalate, hydroxypropyl methyl cellulose acetate succinate, carboxymethyl ethyl cellulose, styrene acrylate copolymer, methacrylate copolymer, maleic anhydride copolymer and shellac, paraffin wax such as paraffin and microcrystalline wax, higher alcohol such as stearyl alcohol and cetanol, and fatty acid ester such as glycerol fatty acid ester, hydrogenated oil, carnauba wax and beeswax, to prepare sustained release preparations. Formulations of syrups can be prepared by mixing with saccharide sweeteners such as sucrose and fructose, sugar alcohol sweeteners such as sorbitol and maltitol, nonsaccharide natural sweeteners such as Stevia extract and glycyrrhizin, and synthetic or semisynthetic sweeteners such as saccharin and aspartame. Other fillers such as cyclodextrin can also be admixed.

As described, oral preparations such as capsules, tablets, granules, fine granules and syrups can be prepared by the known mixing vehicles and mixing formulations.

Ophthalmic solutions will be explained hereinbelow. Examples of aqueous vehicles for ophthalmic solutions include commonly used additives for formulations such as tonicity adjusting agents, buffering agents and preservatives. Examples of the tonicity adjusting agents are sodium chloride, potassium chloride, polyalcohol and saccharide. Examples of buffering agents are sodium borate, sodium citrate, sodium monohydrogenphosphate and sodium dihydrogenphosphate. Examples of preservatives are benzethonium chloride, benzalkonium chloride and chlorobutanol. Further, stabilizers such as glycerol or polysorbate 80 and pH adjusting agents are admixed in necessary.

The ophthalmic solution in the form of ointment, gel and suspension can be prepared by properly formulating the commonly used ointment vehicles, gel vehicles, suspension vehicles, etc.

Inorganic salt or organic salt of morphan derivatives of the present invention are preferable for use in aqueous ophthalmic solution because of their solubility in water.

Injections are explained as follows. The morphan derivatives of the present invention used for injections are preferable in the form of aqueous solution, and use in the form of inorganic salt or organic salt is most preferable. Examples of solvents and/or solubilizing agents as vehicles for injections are glycol such as propylene glycol and glycerol; poly(oxyethylene)-poly(oxypropylene) polymer, glycerol formal, benzyl alcohol and butanediol; vegetable oil such as soy bean oil, cotton seed oil, rapeseed oil and saffron oil; triglyceride of $C_{8-12}$ medium chain fatty acid generally abbreviated as MCT (for example, caprylic acid, capric acid and lauric acid); and mono- or diglyceride of $C_{6-18}$ fatty acid (for example, caproic acid, capric acid, myristic acid, palmitic acid, linoleic acid and stearic acid). Examples of stabilizing agents are cholesterol, tocopherol, albumin, polysaccharide and sodium hydrogensulfite. Example of antiseptic is benzyl alcohol. Examples of emulsifying agents are phospholipids such as egg yolk phospholipid, soybean phospholipid and phosphatidylcholine, and nonionic surface active agents such as polyoxyalkylene polymer (e.g. polyoxyethylene-polyoxypropylene copolymer with mean molecular weight range of 1,000–20,000), hydrogenated castor oil polyoxyethylene-(40)-ether and hydrogenated castor oil polyoxyethylene-(20)-ether. Examples of tonicity adjusting agents, which can be used optionally, are, for example, polyalcohol such as glycerol, sorbitol and xylitol, monosaccharide such as glucose and fructose, disaccharide such as maltose and amino acids such as L-alanine, L-valine and glycine. Examples of emulsifier are, for example, stearic acid, palmitic acid, linoleic acid, linolenic acid or salts thereof, phosphatidylethanol and phosphatidylserine. Aqueous or emulsified injections can be prepared by properly formulating these various vehicles.

Plasters are explained as follows. Vehicles for plasters are properly selected from known polymer vehicles (for example, acrylic composition which is a copolymer with vinyl monomer such as methacrylate, acrylonitrile, vinyl acetate and vinyl propionate; silicone resin; polyisopropylene; polyisobutylene rubber; natural rubber; acrylic rubber; and styrene-butadiene-styrene block copolymer; styrene-isoprene-styrene block copolymer), fat and oil or higher fatty acid (for example, almond oil, olive oil, camellia oil, persic oil, peanut oil, oleic acid, liquid paraffin and polybutene), agents adding stickiness (for example, rosin, rosin denatured maleic acid and hydrogenated rosin ester) and preventive agents for contact dermatitis. To the above vehicles are added the other additives (for example, dl-camphor, 1-menthol, thymol, nonylic acid vanillylamide, capsicum tincture, mentha oil and peppermint oil) if necessary. Then morphan derivatives or salts thereof of the present invention are admixed, together with adding UV absorber or if necessary antioxidant. The resulted mixture is spread over the elastic or nonelastic supporting materials (for example, polypropylene, polyester, polyvinylidene chloride, polyacrylate, polyurethane, rayon, cotton, ethylene-vinyl acetate copolymer, nonwoven fabric and nonwoven paper), and attached with removable coverage to prepare plasters.

Fomentations are explained in the following. Morphan derivatives or salts thereof are added to the fomentation vehicles selected from each vehicle, for example adhesives (for example, synthetic water-soluble polymer such as sodium polyacrylate, polyacrylate, poval, polyvinylpyrrolidone, polyethyleneoxide and polyvinylmethacrylate; natural products such as gum arabic, starch and gelatin; methylcellulose, hydroxypropyl cellulose, alginic acid, sodium alginate, ammonium alginate and carboxymethylcellulose sodium), moistening agents (for example, urea, glycerol propylene glycol, butylene glycol and sorbitol), fillers [for example, kaolin, zinc oxide, talc, titanium, bentonite and epoxy resins, organic acids (such as citric acid, tartaric acid, maleic acid and succinic acid), calcium and aluminum], water, solubilizing agents (for example, propylene carbonate, crotamiton and diisopropyl adipate), agents adding stickiness (for example rosin, ester gum, polybutene and polyacrylic ester), preventive agents for contact dermatitis (for example, diphenhydramine hydrochloride, chlorpheniramine maleate, glycyrrhizic acid, dexamethasone, betamethasone and fluocinolone acetonide) and other additives (for example, 1-menthol, camphor, nonylic acid vanillylamide, thymol, capsicum extract and mentha oil), further UV absorber or if necessary antioxidant are formulated to obtain fomentations.

Ointments can be prepared as follows. Ointment vehicles are selected from conventionally used vehicles. For example, it is preferably to be selected from higher fatty acids or esters thereof (for example, adipic acid, myristic acid, palmitic acid, stearic acid, oleic acid, adipic acid ester, myristic acid ester, palmitic acid ester, lauryl hexylate and ethyl isooctanoate), waxes (for example, spermaceti, yellow beeswax and ceresin), surface active agents (for example, polyoxyethylene alkyl ether phosphate ester), higher alcohol (for example, cetanol, stearyl alcohol and cetostearyl alcohol), silicone oil (for example, dimethylpolysiloxane, dimethylphenylpolysiloxane, glycol methylpolysiloxane and silicone glycol polymer), hydrocarbons (for example, hydrophilic petrolatum, white soft paraffin, purified lanolin and liquid paraffin), water, humectant (for example, glycerol, propylene glycol, butylene glycol and sorbitol), preventive agents for contact dermatitis and other additives (for example, 1-menthol, camphor and mentha oil). Preparations for percutaneous absorption, oral mucosal absorption and suppositories can be prepared by properly formulating these vehicles with morphan derivatives of the present invention or salts thereof.

Next, gel preparations are described below. Gel vehicles are selected from known or conventionally used various vehicles. Examples of gel vehicles are, for example lower alcohol (for example, ethanol, isopropyl alcohol, etc.), water, gelling agents (for example, carboxy vinyl copolymer, hydroxyethylcellulose, ethylcellulose, carboxyethylcellulose, propylene glycol alginate, etc.), neutralizing agents (for example, triethanolamine, diisopropylamine, sodium hydroxide, etc.), surface active agents (for example, sorbitan sesquioleate, sorbitan trioleate, sorbitan monooleate, sorbitan monostearate, sorbitan monolaurylate, polyethyleneglycol monostearate, polyoxyethylenephenyl ether, polyoxyethylenelauryl ether, etc.), preventive agents for contact dermatitis, and other additives (for example, 1-menthol, camphor, mentha oil, etc.). Preparations for percutaneous absorption, oral mucosal absorption and suppositories can be prepared by properly formulating these vehicles with morphan derivatives of the present invention or salts thereof.

Cream preparations are explained as follows. Cream preparations are selected from known or conventionally used various vehicles. Examples of these vehicles are, for example higher fatty acid esters (for example, myristic acid diester, hexyl palmitate, diethyl sebacate, hexyl laurylate, cetyl isooctanate, etc.), lower alcohol (for example, ethanol, isopropanol, etc.), hydrocarbons (for example, liquid paraffin, squalene, etc.), polyalcohol (for example, propyleneglycol, 1,3-butylene glycol, etc.), higher alcohol (for example, 2-hexyldecanol, cetanol, 2-octyldecanol, etc.), emulsifying agents (for example, polyoxyethylene alkyl ethers, fatty acid esters, polyethylene glycol fatty acid esters, etc.), antiseptics (for example, p-hydroxybenzoate esters), preventive agents for contact dermatitis, and other additives (for example, 1-menthol, camphor, mentha oil, etc.). Cream preparations can be prepared by properly formulating these vehicles with morphan derivatives of the present invention or salts thereof as well as admixing UV absorber, or if necessary antioxidant.

Gel cream preparations which have intermediate properties between creams and gels can be prepared by adding creams to gel-vehicles (for example, carboxyvinyl copolymer, hydroxyethylcellulose, hydroxypropylcellulose, ethylcellulose, carboxymethylcellulose, etc.) and neutralizing agents (for example, diisopropanolamine, triethanolamine, sodium hydroxide, etc.), and adjusting pH to 4–8, preferably 5–6.5.

Preparations for percutaneous absorption, oral mucosal absorption and suppositories can be prepared by properly formulating the vehicles of creams or gel creams with morphan derivatives of the present invention or salts thereof.

Liniments are described hereinbelow. The liniments described in the present invention can be prepared by admixing alcohol (for example, monohydric alcohol such as ethanol, propanol and isopropanol, or polyalcohol such as polyethylene glycol, propyleneglycol, butyleneglycol, etc.), water, fatty acid ester (for example, esters of adipic acid, sebacic acid and myristic acid), surface active agents (for example, polyoxyethylene alkyl ether) with the morphan derivatives or salts thereof of the present invention, further adding UV absorber and, if necessary, antioxidant.

Further, neutralizing agents for pH adjustment or agents for adding adhesives such as cetylcellulose, carboxyvinyl alcohol and hydroxypropylcellulose, preventive agents for contact dermatitis, and other additives (for example, 1-menthol, camphor, mentha oil, capsicum extract, nonylic acid vanillylamide, thymol, crotamotin, propylene carbonate, diisopropyladipate, etc.) can be admixed, if necessary, in the liniments described in the present invention.

Suppositories are described as follows. Vehicles for suppositories can optionally be selected from, for example, synthetic oleaginous bases such as cacao butter, hydrogenated peanut oil, hydrogenated coconut oil, polyethyleneglycol, and water soluble bases such as monorhein, tween or pluronic.

Nasal drops are described hereinbelow. Aqueous suspensions are formulated by dissolving, suspending or emulsifying the morphan derivatives or salts thereof of the present invention in water, buffers [for example, Sorensen buffer (Ergeb. Physiol., 12, 393, 1912), Clark-Lubs buffer (J. Bact., 2, 109, 191, 1917), Michaelis buffer (Die Wasserstollionen Komzentralion, p.186, 1914) or Kolthoff buffer (Bio-Chem. Z., 179, 410, 1926)] or aqueous solutions. Oily suspensions are formulated by suspending or emulsifying the morphan derivatives or salts thereof of the present invention in oily vehicles (for example, sesame oil, olive oil, corn oil, soy bean oil, cotton seed oil, peanut oil, lanolin, vaseline, paraffin, silicone oil, medium chain fatty acids, or glycerol or alcohol ester thereof).

Semisolid preparations (ointments, gels or creams) are formulated by using the above ointments, gel or cream vehicles. The liquid preparations are packed in the vessel for nasal application, vessel for spray or vessels suitable for intranasal application, and are applied dropwise or spray intranasally.

Aerosol preparations are formulated by using vehicle composition of propellant such as liquid natural gas, dimethyl ether, carbon dioxide and flon gas and fillers.

Adhesives for oral mucosa are prepared by formulating vehicle compositions, for example, hydrophilic polymer such as hydroxypropylcellulose, acrylic copolymer, carboxyvinyl polymer, polyvinyl pyrrolidone, polyvinyl alcohol, polyethyleneglycol, alginic acid or salts thereof, maleic anhydride—methyl vinyl ether copolymer, chitosan, chitosan derivatives, vinyl acetate copolymer, agar and gelatin, antimicrobial agents, softeners, surface active agents, crosslinking agents, neutralizing buffer, fillers, coloring agents and other fillers to prepare adhesive tablets or oral film adhesives.

Dosages of morphan derivatives or salts thereof described in the present invention, and most especially, the morphan derivatives represented by the formula (1) described earlier (or salts thereof) can be adjusted according to the conditions or actual diseases of the patients, and are usually 0.1–1000 mg/kg, once or twice a day.

Since the morphan derivatives or salts thereof described in the present invention, and most especially, the morphan derivatives represented by the formula (1) described earlier (or salts thereof) can regulate or adjust the activation of glycine receptors, they can be used as drugs for treatment of various nerve diseases and as central nervous system acting drugs such as anesthetics or antitussives. Further, the morphan derivatives or salts thereof described in the present invention have specific actions on glycine receptors, and are useful as drugs with fewer adverse effects. In addition, since the morphan derivatives or salts thereof described in the present invention can specifically regulate the activation of the glycine receptor, these can be a useful pharmacological tool for analyzing the functions of the glycine receptors.

EXAMPLES

Hereinunder, the present invention will be explained by Examples, however, the present invention should not be limited to these Examples.

Example 1

Preparation of 2-Methyl-2-azabicyclo[3.3.1]nonane Shown by the Following Formula:

To a solution (2 ml) of hydrochloric acid salt of 2-azabicyclo[3.3.1]nonane (100 mg, 0.62 mmol) in methanol were added at 35% formalin aqueous solution (1 ml) and 10% palladium on activated carbon (100 mg), and the mixture was stirred for 3 hours at room temperature under the hydrogen atmosphere. The reaction mixture was filtered by means of suction, and after concentration of the filtrate under a reduced pressure, a saturated aqueous solution of sodium bicarbonate (100 ml) was added thereto, followed by extraction with chloroform (3×20 ml). The extrant was dried (over MgSO$_4$), followed by removal of the solvent and purification of the residue with silica gel column chromatography (chloroform-methanol-triethylamine=100:9:1). Thus obtained oily substance was dissolved in a 5% methanol solution (20 ml) of hydrochloric acid, followed by concentration under a reduced pressure, to yield a crude crystal of hydrochloric acid salt (98 mg, 90%), which was recrystallized from hexane to obtain hydrochloric acid salt of 2-methyl-2-azabicyclo[3.3.1]nonane as a yellow needle-like crystal.

Melting point: 147–152° C.;

$^1$H NMR spectrum: (500 MHz, CDCl$_3$) δ; 1.36–1.39 (1H, m), 1.54–1.71 (6H, m), 1.83–1.89 (2H, m), 2.00–2.17 (2H, m), 2.42(3H, s), 278–282 (2H, m), 2.88 (1H, td, J=12.4, 5.1 Hz). $^{13}$C NMR spectrum: (125 MHz, CDCl$_3$) δ; 22.2 (CH$_2$), 24.6 (CH$_2$), 25.2 (CH), 30.5 (CH$_2$), 30.7 (CH$_2$), 34.7 (CH$_2$), 43.3 (CH$_3$), 51.5 (CH$_2$), 53.3 (CH). Electron impact mass spectrum: m/s (relative intensity); 139(M$^+$-HCl, 32), 96(100).

Example 2

Preparation of 2-Ethyl-2-azabicyclo[3.3.1]nonane Shown by the Following Formula:

To a solution (2 ml) of 2-azabicyclo[3.3.1]nonane (100 mg, 0.62 mmol) in methanol were added a 10% acetaldehyde solution (5 ml) and 10% palladium on activated carbon (100 mg) and the mixture was stirred for 3 hours under the hydrogen atmosphere. The reaction mixture was filtered by means of suction, and the filtrate was concentrated under a reduced pressure. A saturated aqueous solution of sodium bicarbonate (10 ml) was added to the residue, followed by extraction with chloroform (3×20 ml). The extrant was dried (over MgSO$_4$), followed by removal of the solvent and purification of the residue with silica gel column chromatography (chloroform-methanol-triethylamine=100:9:1), to obtain 2-ethyl-2-azabicyclo[3.3.1]nonane (68 mg, 72%) as a colorless oily material.

$^1$H NMR spectrum: (400 MHz, CDCl$_3$) δ; 1.12 (3H, t, J=7.2 Hz), 1.30–1.41 (1H, m), 1.52–1.79 (6H, m), 1.83–1.95 (2H, m), 2.00–2.13 (2H, m), 2.63 (2H, q, J=7.2 Hz), 2.79 (1H, td, J=12.2, 5.2 Hz), 2.89–3.01 (2H, m), $^{13}$C NMR spectrum: (100 MHz, CDCl$_3$) δ; 12.4 (CH$_3$), 22.2 (CH$_2$), 25.1 (CH$_2$), 25.8 (CH), 30.4 (CH$_2$), 30.9 (CH$_2$), 34.4 (CH$_2$), 49.3 (CH$_2$), 49.6 (CH$_2$), 50.4 (CH). Electron impact mass spectrum: m/s (relative intensity); 153 (M$^+$, 17), 138 (13), 110 (100).

Example 3

Preparation of 2-Allyl-2-azabicyclo[3.3.1]nonane Shown by the Following Formula:

To a solution (6.5 ml) of 2-azabicyclo[3.3.1]nonane (100 mg, 0.62 mmol) in dimethoxyethane were added allylbromide (105 mg, 0.87 mmol) and potassium carbonate (94 mg, 0.68 mmol) and the mixture was heated at reflux temperature for 3.5 hours. Ether (10 ml) was added to the reaction mixture, followed by filtration and removal of the solvent, and the residue was purified with silica gel column chromatography (chloroform-methanol-triethylamine=100:9:1), to obtain 2-allyl-2-azabicyclo[3.3.1]nonane (52 mg, 51%) as a colorless oily substance.

$^1$H NMR spectrum: (400 MHz, CDCl$_3$) δ; 1.27–1.37 (1H, m), 1.55–2.07 (10H, m), 2.78–2.81 (2H, m), 2.87 (1H, quint, J=3.2 Hz), 3.17 (1H, qdt, J=13.3, 6.5, 1.2 Hz), 5.08 (1H, dddd, J=9.9, 2.0, 1.0, 1.0 Hz), 5.19 (1H, dq, J=17.0, 1.6 Hz), 5.89 (1H, dddd, J=17.0, 9.9, 6.5, 6.5 Hz). $^{13}$C NMR spectrum: (100 MHz, CDCl$_3$) δ; 22.4 (CH$_2$), 25.3 (CH$_2$), 25.8 (CH), 30.7 (CH$_2$), 31.0 (CH$_2$), 34.9 (CH$_2$), 49.6 (CH$_2$), 50.9 (CH), 59.5 (CH$_2$), 116.9 (CH$_2$), 136.5 (CH). Electron impact mass spectrum: m/s (relative intensity); 165 (M$^+$, 11), 122 (100).

Example 4

Preparation of 1-Ethyl-2-azabicyclo[3.3.1]nonane 1-ethyl-2-azabicyclo[3.3.1]nonane was synthesized according to the method for preparing 1-lower alkyl-morphan, disclosed in J. Org. Chem., 62, 8280–8281 (1997).

Example 5

Preparation of 1-Propyl-2-azabicyclo[3.3.1]nonane

1-Propyl-2-azabicyclo[3.3.1]nonane was synthesized according to the method for preparing 1-lower alkyl-morphan, disclosed in J. Org. Chem., 62, 8280–8281 (1997).

Example 6

Preparation of 5-Azatricyclo[6.3.1.0$^{1,5}$]dodecane

5-Azatricyclo[6.3.1.0$^{1,5}$]dodecane was synthesized according to the preparation method disclosed in J. Org. Chem., 62, 8280–8281 (1997).

Example 7

Preparation of 2-{[1-Allyl-(2-propenyl)-2-azabicyclo[3.3.1]nonane-2-yl]methyl}phenol 2-{[1-Allyl-(2-propenyl)-2-azabicyclo[3.3.1]-2-nonenyl]methyl}phenol was synthesized according to the preparation method disclosed in J. Org. Chem., 62, 8280–8281 (1997).

Experimental Example 1

In order to confirm the excellent actions of the derivatives described in the present invention on modification of glycine receptors, the actions of various morphan derivatives against ionic current induced by glycine were evaluated in a single neuron of the tractus solitarius nucleus of a guinea pig. Chemical structures of the compounds used are shown in Table 1.

(1) Experimental Method

The isolation of a single neuron was performed according to the method described in Kay et al. (J. Neurosci. Meth., 16, 227–238, 1986). Guinea pigs, Hartley strain, 7–10 days of age, were anesthetized, bled and decapitated and the medullae were rapidly extracted. Sliced sections, thickness 400 μm, were prepared by using a microslicer. The sliced segments obtained were incubated at 37° C. for 30 minutes, and regions of the tractus solitarius nucleus were punched out under a stereoscope. The punched out specimens were trypsinized in a 100% oxygen atmosphere at 37° C. for 30–60 minutes. The trypsinized tissues were dispersed mechanically to obtain the single neurons. Measurements of the ionic currents activated by glycine were performed using the whole cell mode of the patch clamp method. The ionic currents obtained were recorded using a pen-recorder. Administration of the test compounds was performed by the Y-tube method in which the external fluid peripheral to the cells could be changed to the test drug solution within 2 msec. (Neurosci. Lett., 103, 56–63, 1989). Concentrations of the test compounds were 1 mM, except that the highly lipophilic compound of example 7 was examined at 300 μM. All data were expressed by mean±S.E.

(2) Results

The results of the effects of 7 morphan derivatives on glycine induced currents are shown in Table 1.

TABLE 1

| Experimental No. | Chemical Structure | Action (% of control) |
|---|---|---|
| Compound of Example 1 | CH$_3$ group on N of azabicyclic structure | ± (99.7 ± 1.5%) |
| Compound of Example 2 | CH$_3$–CH$_2$– group on N of azabicyclic structure | + (150.6 ± 14.2%) |
| Compound of Example 3 | allyl group on N of azabicyclic structure | + (138.9 ± 5.6%) |
| Compound of Example 4 | CH$_3$–CH$_2$– group on NH of azabicyclic structure | − (70.9 ± 2.7%) |
| Compound of Example 5 | CH$_3$–CH$_2$–CH$_2$– group on NH of azabicyclic structure | + (138.1 ± 7.0%) |
| Compound of Example 6 | azatricyclic structure | + (152.1 ± 16.6%) |

TABLE 1-continued

| Experimental No. | Chemical Structure | Action (% of control) |
|---|---|---|
| Compound of Example 7 |  | − (60.5 ± 2.7%) |

± no action,
+ potentiated,
− inhibited,
mean ± S.E.

In Table 1, the effects of the morphan derivatives on ionic currents in single neurons from the tractus solitarius nucleus, induced by glycine at 30 μM are summarized.

Figure 1:
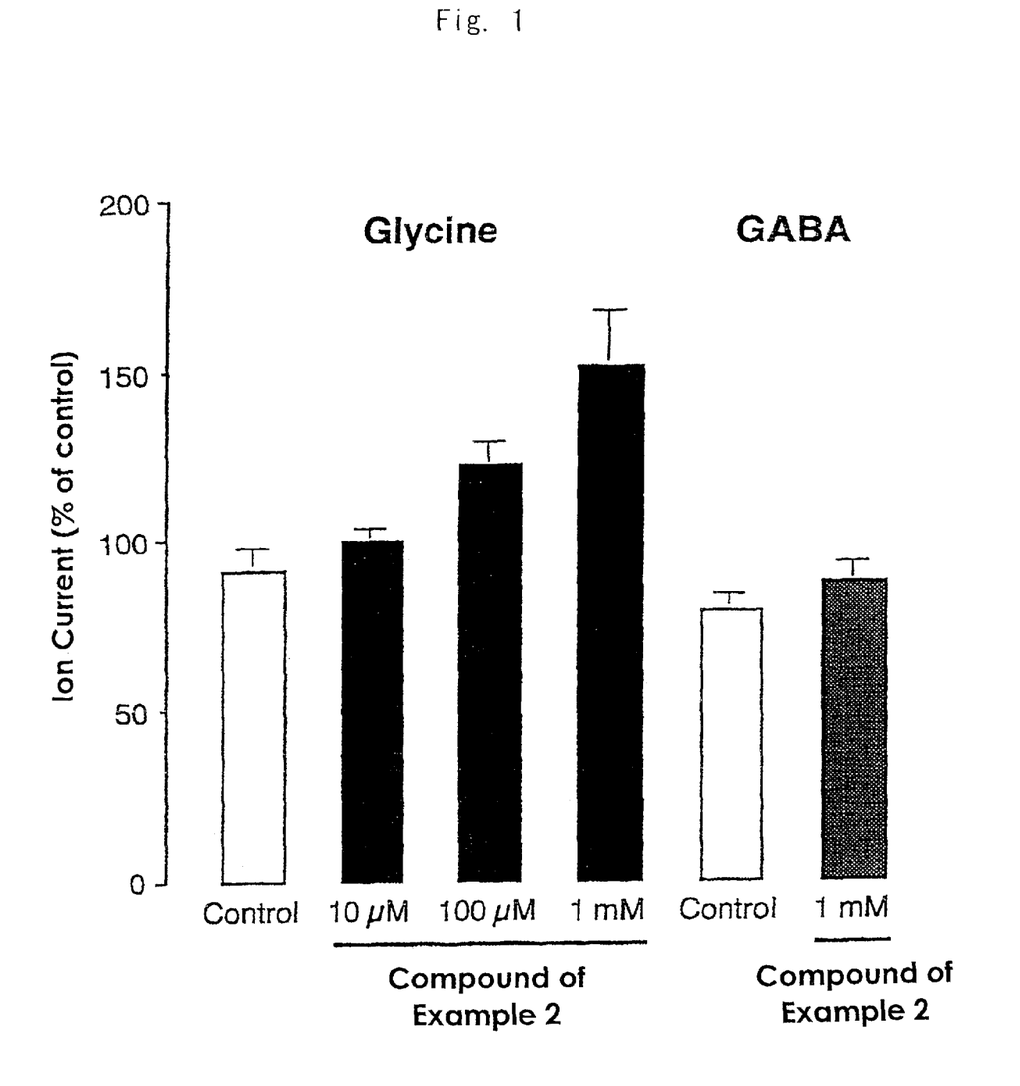
FIG. 1 shows effects of the compound in Example 2, exhibiting the strongest enhancing action, for the ionic current induced by 30 $\mu$M of glycine and 30 $\mu$M of GABA.
Figure 2:
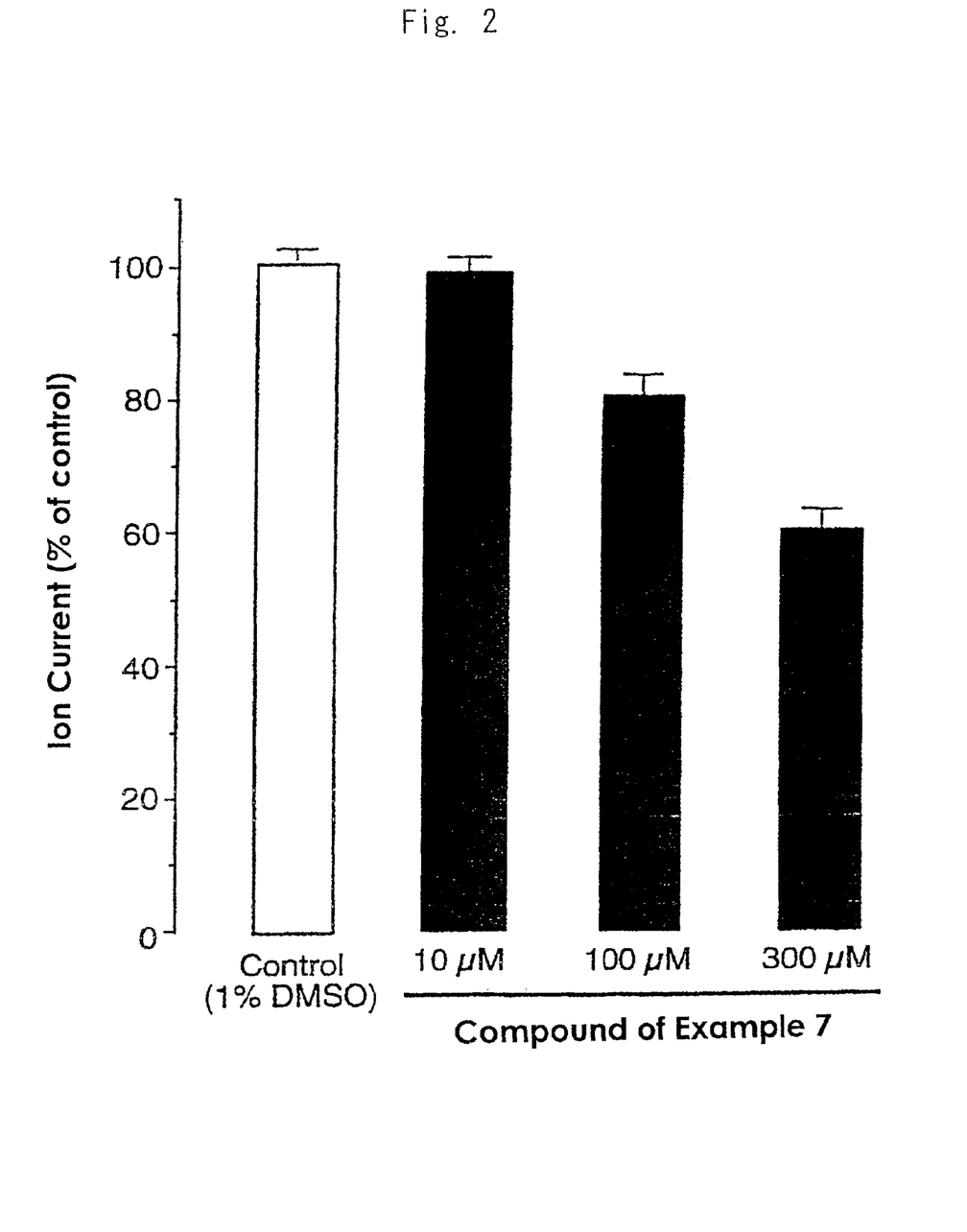
FIG. 2 shows effects of the compound in Example 7, exhibiting the strongest inhibition action, for the current induced by 30 $\mu$M of glycine

The effects of the morphan derivatives on glycine-induced ionic currents were classified into three types: weak action (a compound such as example 1); inhibitory action (compounds such as examples 4 and 7); and potentiation action (compounds such as examples 2, 3, 5 and 6). From among these, the compound shown in example 2 which showed potentiation action on the glycine-induced current; and the compounds which showed inhibitory action were examined further. The compound shown in example 2 potentiated glycine-induced current reversibly within the range from 10 μM–1 mM. On the other hand, the compound shown in example 2 had no action against GABA-induced currents at 1 mM. Consequently, the action of the compound shown in example 2 showed concentration dependency and specificity for potentiation (FIG. 1). The compound shown in example 7 inhibited glycine-induced currents in a concentration-dependent manner within a range from 10–300 μM (FIG. 2).

Examples of the preparations comprising the morphan derivatives or salts thereof, more particularly the morphan derivatives represented by the formula (1) or (2) hereinbefore described in the present invention and the pharmaceutically acceptable carriers are described hereinbelow. Examples of these formulas of pharmaceuticals are only examples and can be modified according to the known method to prepare various formulas of pharmaceuticals.

Formula of Pharmaceutical 1

Aqueous injections can be prepared according to the following mixing formula.

| Compound of example 2 (Na salt) | 1.0 g |
|---|---|
| Benzyl alcohol | 2.0 g |
| Nicotinamide | 3.0 g |
| Propyleneglycol | 40.0 g |
| Distilled water | 100 ml |

Formula of Pharmaceutical 2

Lipid microsphere injections can be prepared according to the following mixing formula.

| Compound of example 4 (Na salt) | 1.0 g |
|---|---|
| JP soybean oil | 21.0 g |
| Purified soy bean phospholipid | 2.5 g |
| Glycerol | 5.0 g |
| Distilled water | 175 ml |

Formula of Pharmaceutical 3

Tablets can be prepared according to the following mixing formula (Total weight 100 wt %).

| Compound of example 2 | 24.0 wt % |
|---|---|
| Crystalline cellulose | 21.0 wt % |
| Lactose | 54.0 wt % |
| Magnesium stearate | 1.0 wt % |

Formula of Pharmaceutical 4

Tablets can be prepared according to the following mixing formula (Total weight 100 wt %).

| Compound of example 3 | 26.0 wt % |
|---|---|
| Crystalline cellulose | 21.0 wt % |
| Lactose | 42.0 wt % |
| Cross povidone | 10.0 wt % |
| Magnesium stearate | 1.0 wt % |

The tablets were spray coated according to the conventional method using coating agents consisting of Eudragit E, ethyl alcohol, water and talc, further spray coated according to the conventional method using coating agents consisting of Eudragit S, ethyl alcohol, water, talc and polyethylene glycol 6000 to prepare the enteric coating preparation disintegrated in the large intestine.

Formula of Pharmaceutical 5

Tablets can be prepared according to the following mixing formula (Total weight 100 wt %).

| Compound of example 7 | 25.0 wt % |
|---|---|
| Fumaric acid | 10.0 wt % |
| Calcium hydrogenphosphate | 40.0 wt % |
| Lactose | 24.0 wt % |
| Talc | 1.0 wt % |

The tablets were spray coated according to the conventional method using liquid coating agents consisting of ethylcellulose, polyvinyl pyrrolidone K30, talc and ethyl alcohol to prepare the sustained release tablets.

Formula of Pharmaceutical 6

Suppositories can be prepared according to the following mixing formula (Total weight 100 wt %).

| Compound of example 4 | 5.0 wt % |
|---|---|
| Polyethyleneglycol | 6.0 wt % |

-continued

| | |
|---|---|
| White beeswax | 10.0 wt % |
| Sorbitan sesquioleate | 4.49 wt % |
| Medium chain fatty acid triglyceride | 74.5 wt % |
| Dibutylhydroxytoluene | 0.01 wt % |

Formula of Pharmaceutical 7

Suppositories can be prepared according to the following mixing formula (Total weight 100 wt %).

| | |
|---|---|
| Compound of example 6 | 5.0 wt % |
| Polyethyleneglycol 400 | 10.0 wt % |
| Polyethyleneglycol 1,000 | 27.0 wt % |
| Polyethyleneglycol 6,000 | 43.5 wt % |
| Propyleneglycol | q.s. |

Formula of Pharmaceutical 8

Ointments can be prepared according to the following mixing formula (Total weight 100 wt %).

| | |
|---|---|
| Compound of example 2 | 5.0 wt % |
| Polyethyleneglycol | 6.5 wt % |
| Isopropyl myristate | 5.5 wt % |
| White soft paraffin | 83.0 wt % |

Formula of Pharmaceutical 9

Ointments can be prepared according to the following mixing formula (Total weight 100 wt %).

| | |
|---|---|
| Compound of example 7 | 5.0 wt % |
| Isopropyl myristate | 12.0 wt % |
| White soft paraffin | 75.0 wt % |
| Spermaceti | 5.0 wt % |
| Polyoxyethylene lauryl ether sodium phosphate | 3.0 wt % |

Formula of Pharmaceutical 10

Liniments can be prepared according to the following mixing formula (Total weight 100 wt %).

| | |
|---|---|
| Compound of example 2 | 3.0 wt % |
| Ethanol | 38.0 wt % |
| 2-hydroxy-4-methoxybenzophenone | 0.5 wt % |
| Propyleneglycol | 13.0 wt % |
| Ethyl sebacate | 3.0 wt % |
| Distilled water | q.s. |
| Sodium hydroxide | 0.07 wt % |

Formula of Pharmaceutical 11

Liniments can be prepared according to the following mixing formula (Total weight 100 wt %).

| | |
|---|---|
| Compound of example 7 | 3.0 wt % |
| Carboxymethylcellulose | 0.1 wt % |
| Purified water | q.s. |
| Polyethylene glycol | 7.0 wt % |

Formula of Pharmaceutical 12

Gel preparations can be prepared according to the following mixing formula (Total weight 100 wt %).

| | |
|---|---|
| Compound of example 2 | 3.0 wt % |
| Diisopropyl adipate | 3.0 wt % |
| Ethanol | 38.5 wt % |
| Carboxyvinyl polymer | 2.0 wt % |
| Distilled water | q.s. |
| Hydroxypropyl cellulose | 2.0 wt % |
| Propylene glycol | 17.0 wt % |
| Diisopropanolamine | 2.5 wt % |

Formula of Pharmaceutical 13

Gel creams can be prepared according to the following mixing formula (Total weight 100 wt %).

| | |
|---|---|
| Compound of example 7 | 3.0 wt % |
| Isopropyl myristate | 11.0 wt % |
| Ethanol | 6.0 wt % |
| Carboxyvinyl polymer | 1.5 wt % |
| Distilled water | q.s. |
| Polyoxyethylene (55) monostearate | 1.0 wt % |
| Coconut oil fatty acid diethanolamide | 4.0 wt % |

Formula of Pharmaceutical 14

Creams can be prepared according to the following mixing formula (Total weight 100 wt %).

| | |
|---|---|
| Compound of example 2 | 5.0 wt % |
| Cetyl alcohol | 12.0 wt % |
| Stearyl alcohol | 2.5 wt % |
| Glycerol monostearate | 6.0 wt % |
| 1,3-butyleneglycol | 13.0 wt % |
| Distilled water | q.s. |

Formula of Pharmaceutical 15

Fomentation can be prepared according to the following mixing formula (Total weight 100 wt %).

| | |
|---|---|
| Compound of example 2 | 3.0 wt % |
| Gelatin | 6.0 wt % |
| Aluminum silicate | 11.0 wt % |
| Polyvinyl alcohol | 4.5 wt % |
| Purified water | q.s. |
| Glycerol | 28.0 wt % |
| Carboxymethylcellulose | 3.0 wt % |

Formula of Pharmaceutical 16

Plasters can be prepared according to the following mixing formula (Total weight 100 wt %).

| | |
|---|---|
| Compound of example 6 | 3.0 wt % |
| Styrene-isoprene-styrene block copolymer (Califlex TR1107, Sell Petrochem. Co.) | 24.5 wt % |
| Liquid paraffin | 43.5 wt % |
| Hydrogenated rosin ester | 29.0 wt % |

Formula of Pharmaceutical 17

Nasal drops can be prepared according to the following mixing formula (Total weight 100 wt %).

| | |
|---|---|
| Compound of example 7 | 10 mg |
| Propyleneglycol | 20 mg |
| Distilled water | (to 100 ml in total) |

INDUSTRIAL APPLICABILITY

As explained above, the morphan derivatives or salts thereof described in the present invention, and most especially, the morphan derivatives represented by the formula (1) described earlier (or salts thereof) can potentiate or inhibit the activation of glycine receptors. Consequently, they can be useful as active ingredients of the medicinal composition for treatment or prevention, i.e. drugs for treatment of various neurological diseases and central nervous system acting drugs such as anesthetics or antitussives. In addition, the morphan derivatives or salts thereof described in the present invention can be a useful pharmacological tool for analyzing the functions of the glycine receptors.

What is claimed is:

1. A pharmaceutical composition comprising a morphan derivative or a salt thereof represented by formula (1) and a pharmaceutically acceptable carrier thereof:

(1)

wherein
$R_1$ is hydrogen, an alkyl group having 1–15 carbon atoms, an alkenyl group having 2–20 carbon atoms, and aralkyl group having 7–12 carbon atoms, each of which is optionally substituted with an alkyl group having 1–15 carbon atoms, an alenyl group having 2–20 carbon atoms, a halogen atom, a hydroxy group, or a lower alkoxy group having 1–15 carbon atoms;

$R_2$ is hydrogen, an alkyl group having 1–15 carbon atoms or an alkenyl group having 2–20 carbon atoms; or $R_1$ and $R_2$ taken together form an alkylene group having 2–20 carbon atoms, wherein at least one of $R_1$ and $R_2$ is not hydrogen.

2. A morphan derivative or a salt thereof represented by the following formula (2):

(2)

wherein, $R_1$ is a hydrogen, an alkyl group having 1–15 carbon atoms, an alkenyl group having 2–20 carbon atoms, an aralkyl group having 7–12 carbon atoms, each of which is optionally substituted with an alkyl group having 1–15 carbon atoms, an alkenyl group having 2–20 carbon atoms, a halogen atom, a hydroxyl group, or a lower alkoxy group having 1–15 carbon atoms;

$R_2$ is a hydrogen, an alkyl group having 1–15 carbon atoms, or an alkenyl group having 2–20 carbon atoms; or $R_1$ and $R_2$ taken together form an alkylene group having 2–20 carbon atoms, wherein when $R_1$ is hydrogen then $R_2$ is not hydrogen or an alkyl group.

3. A method for treatment of a disease caused by dysfunction of glycine receptor activation, the method comprising the step of:

administrating to a patient having disease caused by dysfunction of glycine receptor activation an effective amount of a morphan derivative or a salt thereof represented by formula (1):

(1)

wherein, $R_1$ is hydrogen, an alkyl group having 1–15 carbon atoms, an alkenyl group having 2–20 carbon atoms, and aralkyl group having 7–12 carbon atoms, each of which is optionally substituted with an alkyl group having 1–15 carbon atoms, an alkenyl group having 2–20 carbon atoms, a halogen atom, a hydroxy group, or a lower alkoxy group having 1–15 carbon atoms;

$R_2$ is hydrogen, an alkyl group having 1–15 carbon atoms or an alkenyl group having 2–20 carbon atoms; or $R_1$ and $R_2$ taken together form an alkylene group having 2–20 carbon atoms; and a pharmaceutically acceptable carrier.

4. The method of claim 3, wherein the disease caused by dysfunction of glycine receptor activation is selected from convulsive seizures, epileptic seizures, nonketotic hyperglycinemia, or diseases and disorders which are suitable for treatment with at least pharmaceutical agent selected from anesthetics, anti-tussives, or central nervous system stimulants.

* * * * *